(12) United States Patent
Tripathi et al.

(10) Patent No.: US 10,717,083 B2
(45) Date of Patent: Jul. 21, 2020

(54) MICRODEVICE FOR SEPARATING PLASMA FROM HUMAN BLOOD

(71) Applicant: Indian Institute of Technology, Bombay, Mumbai (IN)

(72) Inventors: Siddhartha Tripathi, Maharashtra (IN); Venkatabala Varunkumar Yeachana, Maharashtra (IN); Amit Agrawal, Maharashtra (IN)

(73) Assignee: INDIAN INSTITUTE OF TECHNOLOGY, BOMBAY, Mumbai (IN)

( * ) Notice: Subject to any disclaimer, the term of this patent is extended or adjusted under 35 U.S.C. 154(b) by 190 days.

(21) Appl. No.: 15/565,515

(22) PCT Filed: Jun. 24, 2016

(86) PCT No.: PCT/IN2016/000166
§ 371 (c)(1),
(2) Date: Oct. 10, 2017

(87) PCT Pub. No.: WO2017/179064
PCT Pub. Date: Oct. 19, 2017

(65) Prior Publication Data
US 2018/0207637 A1 Jul. 26, 2018

(30) Foreign Application Priority Data
Apr. 11, 2016 (IN) .............................. 201621012710

(51) Int. Cl.
*B01L 3/00* (2006.01)
*B01D 21/26* (2006.01)
(Continued)

(52) U.S. Cl.
CPC ........ *B01L 3/502753* (2013.01); *B01D 21/26* (2013.01); *B01L 3/00* (2013.01);
(Continued)

(58) Field of Classification Search
CPC ................. B01L 3/502753; B01L 3/00; B01L 2400/0409; B01L 2300/0883;
(Continued)

(56) References Cited

U.S. PATENT DOCUMENTS

2009/0283483 A1\* 11/2009 Achard .............. B01D 21/0012
210/802
2012/0152858 A1 6/2012 Yang
(Continued)

FOREIGN PATENT DOCUMENTS

IN 2344/MUM/2013 A \* 6/2015

OTHER PUBLICATIONS

AMINI 2014 "Inertial microfluidic physics" Lab Chip, 14, 2739-2761 (Year: 2014).\*
(Continued)

*Primary Examiner* — Liam Royce
(74) *Attorney, Agent, or Firm* — Tim Tingkang Xia, Esq.; Locke Lord LLP

(57) ABSTRACT

A microdevice for separating plasma from human blood comprising a blood flow channel (2) connected to a corpuscles flow channel (5) and a plasma flow channel (8) through a curved construction channel (15). Blood flow channel has width 150 to 400 μm and length 1-20mm, constriction channel (15) has width 60 to 200 μm, length 0.157 to 3.15mm and curvature angle 90-270° with inner radius 50 μm to 1mm and outer radius 110 μm to 1.2 mm and corpuscles flow channel (5) has width 200 to 700 μm, length 0.5 to 5mm and bend angle 40-70°. Plasma channel is sinewave shaped and has width 20-150 μm and length 10-50mm. Channels have uniform depth 20-120 μm (FIG. 1).

10 Claims, 2 Drawing Sheets

(51) Int. Cl.
*G01N 30/26* (2006.01)
*G01N 33/49* (2006.01)
*G01N 30/38* (2006.01)

(52) U.S. Cl.
CPC ............ *G01N 30/26* (2013.01); *G01N 30/38* (2013.01); *G01N 33/491* (2013.01); *B01L 2300/0864* (2013.01); *B01L 2300/0883* (2013.01); *B01L 2400/0409* (2013.01)

(58) Field of Classification Search
CPC B01L 2300/0864; G01N 30/38; G01N 30/26; G01N 33/491; B01D 21/26
See application file for complete search history.

(56) References Cited

U.S. PATENT DOCUMENTS

| | | |
|---|---|---|
| 2012/0276544 A1 | 11/2012 | Quake et al. |
| 2013/0008240 A1 | 1/2013 | Ito et al. |
| 2014/0216179 A1 | 8/2014 | Shinoda et al. |
| 2014/0287509 A1 | 9/2014 | Sharei et al. |
| 2015/0238963 A1* | 8/2015 | Han .................. B01D 21/0012 210/802 |

OTHER PUBLICATIONS

United States Patent and Trademark Office (ISR/US), "International Search Report for PCT/IN2016/000166", US, dated Nov. 4, 2016.
Kersaudy-Kerhoas et al., "Validation of a blood plasma separation system by biomarker detection", The Royal Society of Chemistry, Lab Chip, 2010, vol. 10, pp. 1587-1595.
Blatter et al., "Separation of Blood in Microchannel Bends", Proceedings of SPIE, 2004, vol. 5345, pp. 17-25.
Tripathi et al., "Blood plasma separation in elevated dimension T-shaped microchannel", Biomed Microdevices, 2013, vol. 15, pp. 415-425.
Prabhakar et al., "A novel, compact and efficient microchannel arrangement with multiple hydrodynamic effects for blood plasma separation", Microfluid Nanofluid, Oct. 9, 2014.
Tripathi, S. et al., "Performance study of microfluidic devices for blood plasma separation—a designer's perspective", Journal of Micromechanics and Microengineering, 2015, 25(8), pp. 1-15.
Tripathi, S. et al., "Passive blood plasma separation at the microscale: a review of design principles and microdevices", Journal of Micromechanics and Microengineering, 2015, 25(8), pp. 1-24.
Tripathi, S., "Blood Plasma Separation & Hydrodynamic Flow Focusing in Microchannels", PhD Thesis, 2017.
Tripathi, S. et al., "Microdevice for plasma separation from whole human blood using bio-physical and geometrical effects", Scientific Reports, 2016, vol. 6, pp. 1-15.

\* cited by examiner

MICRODEVICE FOR SEPARATING PLASMA FROM HUMAN BLOOD

FIELD OF THE INVENTION

This application relates to a microdevice for separating plasma from human blood.

This application also relates to a mold for casting the open microchannel pattern of the microdevice.

This application is concerned with improvements in the microdevice and mold as described in our patent application No. 2344/MUM/2013 Filed on 12 Jul. 2013 which is incorporated herein in its entirety by this reference for brevity and which constitutes a part of this application. This application should be read and understood in conjunction with application No. 2344/MUM/2013 in its entirety as a part hereof.

BACKGROUND OF THE INVENTION

Human blood is composed of cellular components (RBCs, WBCs and platelets) and plasma. Plasma comprises bio-markers or analytes which contain several health related important information of human beings. Therefore, plasma separation from human blood is very useful for diagnosis of diseases in human beings. Microfluidic devices are used for separating plasma from human blood.

Microfluidic devices are broadly classified into two main groups or categories, namely active microdevices and passive microdevices. Active microdevices require external forces for their operation, whereas passive microdevices do not require external forces for their operation. Passive microdevices are subclassified into several subcategories. Hydrodynamic microdevices are a subclass of passive microdevices which make use of bio-physical effects, microchannel geometry and flow rates for their operation. Besides having the advantage of not requiring external force for their operation, dynamic passive microdevices have further advantages such as ease of fabrication, simplicity of design and potential to provide clog-free, continuous operation.

Kerhoas et al teach a microdevice comprising a main channel having width 100 µm and depth 20 µm and 8 plasma channels placed at an angle of 45° to the main channel. Two microdevices of plasma channel widths of 20 µm and 10 µm and depth 20 µm are reported. In the case of the microdevice having plasma channel width of 10 µm, a plasma separation efficiency of 99% is reported with whole human blood (haematocrit content 45%) at a flow rate of 2 ml/hr. Plasma yield is reported to be 5% [Kersaudy-Kerhoas, M., Kavanagh, D. M., Dhariwal, R. S., Campbell, C. J., & Desmulliez, M. P. (2010). Validation of a blood plasma separation system by biomarker detection. Lab on a Chip, 10(12), 1587-1595].

Blattert et al teach a microdevice comprising a main channel having bend angle of 90° and bend radius of 500 µm. The width of the main channel is varied between 20 µm to 100 µm. A microdevice of inlet width 42 µm, outlet width 97 µm, plasma channel width 28 µm and depth 116 µm and flow rate ratio of 0.03 (the ratio of the flow rate in the plasma channel to the flow rate in the blood outlet) is reported to give a plasma separation efficiency of 58% and 90% with blood hematocrit content of 45% and 5%, respectively at a feed velocity of 2 m/s. Plasma yield is reported to be 5-10% [Blattert, C., Jurischka, R., Schoth, A., Kerth, P., & Menz, W. (2004, Jan.). Separation of blood in microchannel bends. In Micromachining and Microfabrication (pp. 17-25). International Society for Optics and Photonics].

Tripathi et al teach a T-shaped microdevice comprising a main channel of width 400 µm and depth 50 µm and a plasma channel of width of 100 µm and depth of 50 µm. At a flow rate of 0.15 ml/min, flow rate ratio of 54:1 and haematocrit content of 45%, a plasma separation efficiency of 45% and a plasma yield of 1.91% are reported. At the same flow rate and flow ratio and haematocrit content of 2%, a plasma separation efficiency of 99% is reported [Tripathi, S., Prabhakar, A., Kumar, N., Singh, S. G., & Agrawal, A. (2013). Blood plasma separation in elevated dimension T-shaped microchannel. Biomedical microdevices, 15(3), 415-425].

Prabhakar et al teach a hybrid microdevice comprising a microchannel having inlet width 200 µm and depth 60 µm and a plasma channel width 100 µm and depth 60 µm. A plasma separation efficiency of 100% is reported using diluted blood of haematocrit content 15% and a plasma separation efficiency of 80% is reported with whole human blood of haematocrit content 45% at a flow rate of 0.4 ml/min. Plasma yield is reported to be 3% with whole human blood. [Prabhakar, A., Kumar, Y.V.B.V., Tripathi, S., & Agrawal, A. (2014). A novel, compact and efficient microchannel arrangement with multiple hydrodynamic effects for blood plasma separation. Microfluidics and Nanofluidics, 18(5-6), 995-1006].

Although numerous microdevices for separating plasma from human blood are known and reported, they are mostly for separating plasma from diluted blood. This involves the step of dilution of the blood prior to plasma separation. The plasma separation efficiency of the microdevices in general is poor and decreases as the hematocrit content in the blood increases. Besides, the microdevices comprise microchannels having very small dimensions in the range of microns. As a result, they are difficult and expensive to fabricate and are at risk of clogging leading to failure and discontinuous operation of the microdevices. During dilution, there are chances for the biomarkers to get lost. When a biosensor is integrated with a microdevice using diluted blood, the sensitivity of the microsensor is reduced due to the diluted blood. Accuracy of diagnosis using biomarkers depends on the concentration of biomarkers in the plasma. The higher the concentration of biomarkers, the better the accuracy of diagnosis. Therefore, use of whole blood (with hematocrit of about 42% or more) for plasma separation is advantageous to get high concentrations of biomarkers in the plasma. Use of whole blood is also advantageous in that it eliminates the step of blood dilution. Microdevices having high plasma separation efficiency are advantageous and desirable.

There is thus scope and need for microdevices for separation of plasma from human blood, which are very efficient and effective in plasma separation from human blood having a wide range of hematocrit (Hct) content, especially whole blood and which have other advantages and benefits such as ease of fabrication, simplicity of design, clog free and continuous operation and capability of being easily integrated with biosensors.

DESCRIPTION OF THE INVENTION

While carrying out further research and development on the microchannel pattern of the microdevice and mold described in our patent application No. 2344/MUM/2013 with a view to improve the plasma separation efficiency of the microdevice from human blood, we have found out that the microchannel pattern having certain geometric design and configuration and dimensional parameters will give significantly and substantially improved plasma separation efficiency with human blood having a wide range of Hct content, besides giving several other advantages and benefits.

According to the invention there is provided a microdevice for separating plasma from human blood, comprising a polymer material microchip having a microchannel pattern comprising a blood flow channel having a blood inlet end and a blood outlet end, a corpuscles flow channel having a corpuscles inlet end and a corpuscles outlet end and at least one plasma flow channel having a plasma inlet end and a plasma outlet end, the blood inlet end of the blood flow channel being connected to a blood reservoir, the corpuscles outlet end of the corpuscles flow channel being connected to a corpuscles reservoir and the plasma outlet end of the plasma flow channel being connected to a plasma reservoir, the blood outlet end of the blood flow channel being connected to the corpuscles inlet end of the corpuscles flow channel and plasma inlet end of the plasma flow channel through a curved constriction channel having one end connected to the blood outlet end of the blood flow channel and the other end connected to the corpuscles inlet end of the corpuscles flow channel and plasma inlet end of the plasma channel, wherein the other end of the constriction channel is contiguous with the plasma inlet end of the plasma flow channel, the corpuscles flow channel is angular having one limb with the corpuscles inlet end terminating into the constriction channel perpendicular thereto and the other limb having the corpuscles outlet end connected to the corpuscles reservoir, the blood flow channel has a width of 150 to 400 µm and a length of 1-20 mm, the constriction channel has a width of 60 to 200 µm and a length of 0.157 to 3.15 mm, and an angle of curvature 90-270° with an inner radius of 50 µm to 1 mm and an outer radius of 110 µm to 1.2 mm, the corpuscles flow channel has a width of 200 to 700 µm and a length of 0.5 to 5 mm and a bend angle of 40-70° and the plasma channel has a width of 20-150 µm and a length of 10-50 mm and the blood flow channel, corpuscles flow channel, plasma flow channel and constriction channel each has uniform depth of 20-120 µm.

Because of the unique geometric design and configuration and dimensional parameters of the microchannel pattern of the invention, a combination of biophysical effects and geometrical effects come into play during functioning of the microdevice to facilitate clog free continuous and smooth operation of the microdevice and to separate plasma from human blood, especially whole human blood (with hematocrit content of about 42% or more), very effectively and efficiently for a wide range of hematocrits or hematocrit contents in the blood. As the plasma separation efficiency is increased plasma quality is improved so as to enrich the plasma with high quality biomarkers to facilitate better diagnosis. The microdevice of the invention avoids the step of dilution when used to separate plasma from whole blood and does not affect the sensitivity of the biosensor as and when integrated therewith.

Besides, the dimensional parameters of the microchannel pattern of the invention are sufficiently large for the microchannel pattern to be easily fabricated and easily scaled up to industrial level for fabrication at industrial scale. The microdevice of the invention does not require any external forces for its operation and has also other advantages such as simplicity of design, clog-free and continuous operation and capability of being easily integrated with biosensors.

DESCRIPTION OF THE EMBODIMENTS OF THE DRAWINGS

Figure 1:
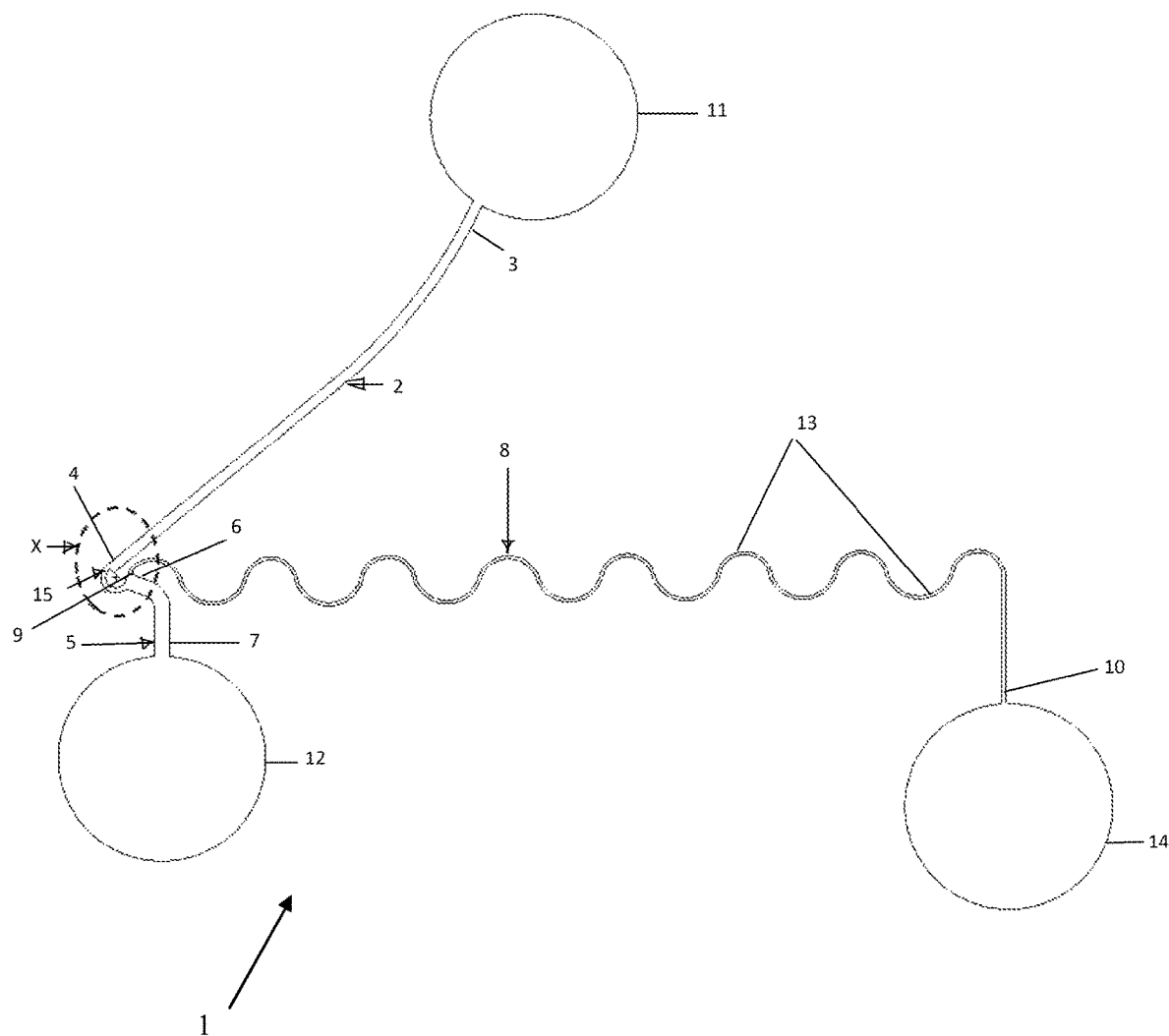
FIG. 1 of the accompanying drawings is a schematic view of the microchannel pattern of a microdevice for separating plasma from human blood according to an embodiment of the invention.
Figure 2:
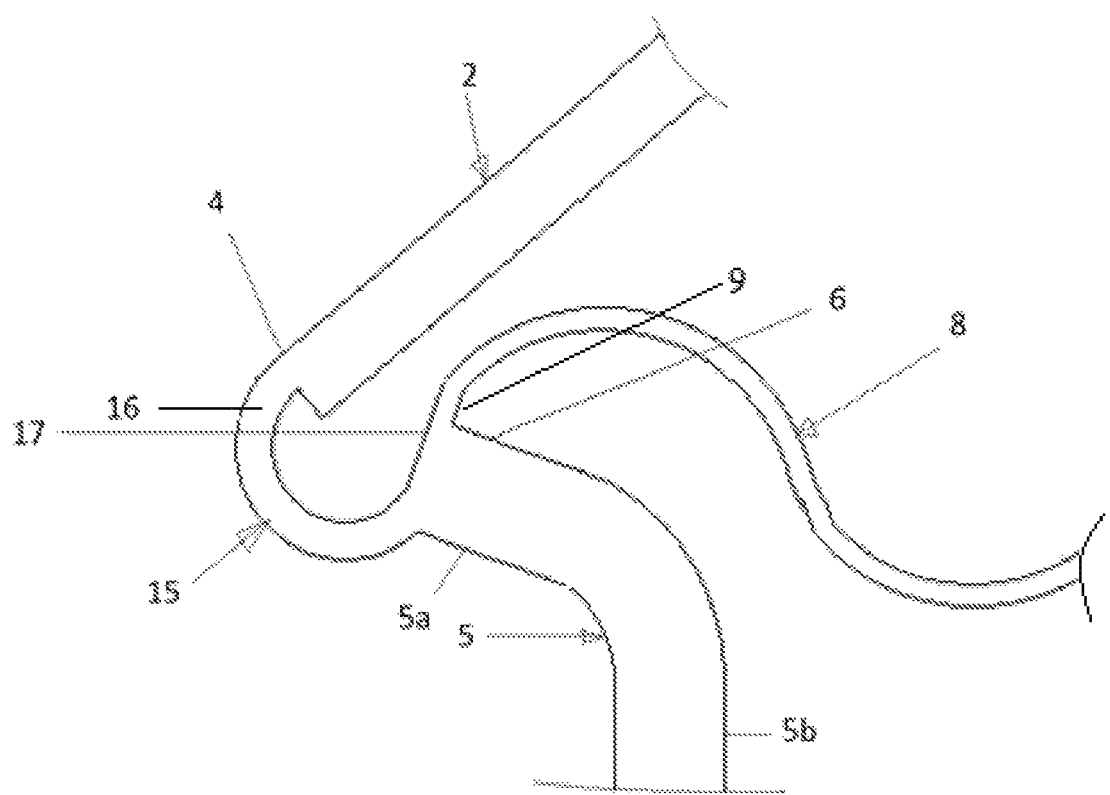
FIG. 2 is an enlarged schematic view at X in FIG. 1.

The microchannel pattern 1 of a microdevice for separating plasma from human blood (not shown) as illustrated in FIGS. 1 and 2 of the accompanying drawings comprises a blood flow channel 2 having a blood inlet end 3 and a blood outlet end 4.5 is a corpuscles flow channel having a corpuscles inlet end 6 and a corpuscles outlet end 7.8 is a plasma flow channel having a plasma inlet end 9 and a plasma outlet end 10. The blood inlet end of the blood flow channel is connected to blood reservoir 11. The corpuscles outlet end of the corpuscles flow channel is connected to corpuscles reservoir 12. The plasma flow channel is sinewave (marked 13) shaped and the plasma outlet end of plasma flow channel is connected to a plasma reservoir 14. The blood outlet end of the blood flow channel is connected to the corpuscles inlet end of the corpuscles flow channel and plasma inlet end of the plasma flow channel through a curved constriction channel 15 having one end 16 connected to the blood outlet of the blood flow channel and the other end 17 connected to the corpuscles inlet end of the corpuscles flow channel and plasma inlet end of the plasma channel.

According to the invention, the other end 17 of the constriction channel is contiguous with the plasma inlet end 9 of the plasma flow channel. The corpuscles flow channel is angular having one limb 5a with the corpuscles inlet end 6 terminating into the constriction channel perpendicular thereto and other limb 5b having the corpuscles outlet end 7 connected to the corpuscles reservoir. The blood flow channel, corpuscles flow channel, constriction channel and plasma flow channel are preferably rectangular or square in cross-section.

According to the invention the microchannel geometry and dimensions of the microchannel pattern are selected such that the blood flow channel has a width of 150 to 400 µm and a length of 1-20 mm. The constriction channel has a width of 60-200 µm and a length of 0.157 to 3.15 mm and angle of curvature 90-270° with an inner radius of 50 µm to 1 mm and an outer radius of 110 µm to 1.2 mm. The corpuscles flow channel has a width of 200 to 700 µm and a length of 0.5 to 5 mm and a bend angle of 40-70°. The plasma channel has a width of 20-150 µm and a length of 10-50 mm. The blood flow channel, corpuscles flow channel, plasma flow channel and constriction channel each has uniform depth of 20-120 µm.

In operation of the microdevice of the invention, due to the geometry and dimensions of the microchannel pattern, especially those of the constriction channel (defining a constriction zone), the plasma flow channel and the corpuscles flow channel, the magnitude of the centrifugal forces developed in the constriction channel is substantially increased and resistance to plasma flow in the plasma flow channel is substantially increased and flow rate ratio (the ratio of the flow rate in the plasma flow channel to the flow rate in the corpuscles flow channel) is substantially increased so as to significantly improve the plasma separation efficiency of the microdevice of the invention. According to a preferred embodiment of the invention as illustrated in FIGS. 1 and 2, the one end of the constriction channel is connected to the outer side of the blood outlet of the blood flow channel because of which the outlet end of the blood flow channel provides increased cell free region for the plasma content of the blood to flow smoothly through the constriction channel to improve the plasma separation efficiency of the microdevice.

However, the one end of the constriction channel also can be connected at the centre of the blood outlet end of the blood flow channel. The plasma flow channel need not be sinewave shaped. There can be more than one plasma flow channel. The microchannel pattern can be fabricated using known techniques including 3-D printing. Such variations in the microchannel pattern of the invention are to be construed and understood to be within the scope of the invention.

The following experimental Example is illustrative of the invention but not limitative of the scope thereof.

EXAMPLE 1

A typical microdevice of FIGS. 1 and 2 according to the invention having the following parameters was used to study comparative performance:

All the flow channels were rectangular in cross-section. The width and length of the blood flow channel were 200 μm and 10.2 mm, respectively. The constriction channel had a width of 100 μm and a length of 0.785 mm, and an angle of curvature 180° with an inner radius of 200 μm and an outer radius of 300 μm. The corpuscles flow channel had a width of 300 μm, a length of 1.62 mm and a bend angle of 50°. The plasma channel had a width of 60 μm and a length of 30.26 mm. The blood flow channel, corpuscles flow channel, plasma flow channel and constriction channel each had a uniform depth of 60 μm.

The performance of the typical microdevice of the invention was compared with the typical microdevice of Example 1 of application No 2344/MUM/2013 using blood drawn from 4 healthy volunteers, pretested for any communicable diseases, and mixed with the anticoagulant EDTA (ethylene diamine tetraaceticacid).

Experiments were conducted with whole blood and blood diluted with saline (0.9% NaCl) as the diluting agent in varying quantities to obtain diluted blood samples of varying hematocrit (Hct) contents. The blood flow rates in the microdevice ranged from 0.3 to 0.5 ml/min. Hemocytometer (Neubauer chamber) was used to quantify the plasma content and to carry out the cell count in the experiments. All the experiments were conducted within 3 hours of the blood collection.

Plasma separation efficiency 'n' of the microdevices was calculated using the equation:

$$n = \frac{(Cs - Cp)}{Cs} \times 100,$$

wherein Cs is the number of cells per μL of blood at the inlet end of the blood flow channel and Cp is the number of the cells per μL of plasma at the outlet of the plasma flow channel. Plasma yield is the ratio of extracted plasma volume to inlet volume of blood.

The results were as shown in the flowing Table:

TABLE

| Microdevice | Hct content in the blood | Plasma separation efficiency | Plasma Yield |
| --- | --- | --- | --- |
| 2344/MUM/2013 | 5%, 16%, 24% and 45% | 100%, 100%, 100%, and 75% | 3% with Hct 45% |
| Invention | 7%, 24%, 31% and 42% | 100%, 100%, 99.8%, 99.55% | 1% with Hct 42% |

The results show that the microdevice of 2344/MUM/2013 gave a plasma separation efficiency of 75% with whole human blood (Hct 45%) and that the microdevice of the invention gave a plasma separation efficiency of 99.55% with whole human blood (Hct 42%). It is quite evident from the Table that the microdevice of the invention has significantly improved plasma separation efficiency. Plasma yield is known to reduce with increase in plasma separation efficiency as yield and separation efficiency counteract each other. The low yield in the Table is indicative of the improved separation efficiency of the microdevice of the invention.

We claim:

1. A microdevice for separating plasma from whole blood, comprising a polymer material microchip having a microchannel pattern comprising:
a blood flow channel having a blood inlet end and a blood outlet end;
a corpuscles flow channel having a corpuscles inlet end and a corpuscles outlet end; and
at least one plasma flow channel having a plasma inlet end and a plasma outlet end, the blood inlet end of the blood flow channel being connected to a blood reservoir, the corpuscles outlet end of the corpuscles flow channel being connected to a corpuscles reservoir and the plasma outlet end of the plasma flow channel being connected to a plasma reservoir, the blood outlet end of the blood flow channel being connected to the corpuscles inlet end of the corpuscles flow channel and plasma inlet end of the plasma flow channel through a curved constriction channel having one end connected to the blood outlet end of the blood flow channel and the other end connected to the corpuscles inlet end of the corpuscles flow channel and plasma inlet end of the plasma channel;
wherein the other end of the constriction channel is contiguous with the plasma inlet end of the plasma flow channel, the corpuscles flow channel is angular having one limb with the corpuscles inlet end terminating into the constriction channel perpendicular thereto and the other limb having the corpuscles outlet end connected to the corpuscles reservoir;
wherein the blood flow channel has a width of 150 to 400 μm and a length of 1-20 mm;
wherein the constriction channel has a width of 100 μm and a length of 0.785 mm, and an angle of curvature 180° with an inner radius of 200 μm and an outer radius of 300 μm;
wherein the corpuscles flow channel has a width of 200 to 700 μm and a length of 0.5 to 5 mm and a bend angle of 40-70°;
wherein the plasma flow channel has a width of 60 μm and a length of 10 -50 mm; and
wherein each of the blood flow channel, the corpuscles flow channel, the plasma flow channel and the constriction channel each has a uniform depth of 20-120 μm.

2. The microdevice as claimed in claim 1,
wherein the blood flow channel has the width of 200 μm and the length of 10.2 mm;
wherein the corpuscles flow channel has the width of 300 m, the length of 1.62 mm and the bend angle of 50°;
wherein the plasma flow channel has the length of 30.26 mm; and
wherein each of the blood flow channel, the constriction channel, the corpuscles flow channel and the plasma flow channel has the uniform depth of 60 μm.

3. The microdevice as claimed in claim 1, wherein the blood flow channel, the corpuscles flow channel, the constriction channel and the plasma flow channel are rectangular or square in cross-section.

4. The microdevice as claimed in claim 1, wherein the one end of the constriction channel is connected to the outer side of the blood outlet end of the blood flow channel.

5. The microdevice as claimed in claim 1, wherein each of the blood reservoir, the corpuscles reservoir and the plasma reservoir is circular shaped.

6. The micro device as claimed in claim 5, wherein each of the blood reservoir, the corpuscles reservoir and the plasma reservoir has a diameter 0.5 to 5 mm.

7. The micro device as claimed in claim 6, wherein each of the blood reservoir, the corpuscles reservoir and the plasma reservoir has the diameter of 4 mm.

8. A mold for casting the microchannel pattern of a microdevice for separating plasma from human blood as claimed in claim 1.

9. The microdevice as claimed in claim 2, wherein the blood flow channel, the corpuscles flow channel, the constriction channel and the plasma flow channel are rectangular or square in cross-section.

10. A mold for casting the microchannel pattern of a microdevice for separating plasma from human blood as claimed in claim 2.

\* \* \* \* \*